(12) United States Patent
Fix et al.

(10) Patent No.: US 9,080,967 B2
(45) Date of Patent: Jul. 14, 2015

(54) ELECTRONIC COMPONENT FOR HIGH TEMPERATURES

(75) Inventors: Richard Fix, Gerlingen (DE); Markus Widenmeyer, Schoenaich (DE)

(73) Assignee: ROBERT BOSCH GMBH, Stuttgart (DE)

( * ) Notice: Subject to any disclaimer, the term of this patent is extended or adjusted under 35 U.S.C. 154(b) by 289 days.

(21) Appl. No.: 12/931,496

(22) Filed: Feb. 1, 2011

(65) Prior Publication Data

US 2011/0193140 A1    Aug. 11, 2011

(30) Foreign Application Priority Data

Feb. 4, 2010   (DE) .......................... 10 2010 001 568

(51) Int. Cl.
*G01N 27/414*      (2006.01)

(52) U.S. Cl.
CPC .................................... *G01N 27/414* (2013.01)

(58) Field of Classification Search
CPC ...... G01N 27/4145; G01N 21/78; H01M 8/08
USPC .............................. 257/253, 532; 430/270.13
See application file for complete search history.

(56) References Cited

U.S. PATENT DOCUMENTS

| | | | | |
|---|---|---|---|---|
| 4,654,197 A | * | 3/1987 | Lilja et al. ................. | 204/403.02 |
| 5,973,050 A | * | 10/1999 | Johnson et al. ............... | 524/439 |
| 2002/0015914 A1 | * | 2/2002 | Miyamoto et al. ....... | 430/270.13 |
| 2002/0096737 A1 | * | 7/2002 | Nakamura et al. ............ | 257/532 |
| 2006/0160330 A1 | * | 7/2006 | Kobayashi et al. ........... | 438/460 |
| 2007/0178365 A1 | * | 8/2007 | Sugimasa et al. ............... | 429/44 |
| 2008/0057381 A1 | * | 3/2008 | Jang et al. ....................... | 429/46 |

FOREIGN PATENT DOCUMENTS

| | | |
|---|---|---|
| EP | 0 237 277 | 9/1987 |
| WO | WO 2010/031609 | 3/2010 |

OTHER PUBLICATIONS

"A study of platinum electrode patterning in a reactive ion etcher," J. Vac. Sci. Technol. A 16(3), May/Jun. 1998, pp. 1489-1496.

\* cited by examiner

*Primary Examiner* — Kenneth Parker
*Assistant Examiner* — Fang-Xing Jiang
(74) *Attorney, Agent, or Firm* — Kenyon & Kenyon LLP

(57) ABSTRACT

A chemically sensitive field effect transistor includes a substrate, a conductor track structure situated on the substrate, and a functional layer which is contacted via the conductor track structure. To be able to form a thin, oxidation-stable and temperature-stable conductor track structure, the conductor track structure is made of a metal mixture which includes platinum and one or more metals selected from the group made up of rhodium, iridium, ruthenium, palladium, osmium, gold, scandium, yttrium, lanthanum, the lanthanides, titanium, zirconium, hafnium, niobium, tantalum, chromium, tungsten, rhenium, iron, cobalt, nickel, copper, boron, aluminum, gallium, indium, silicon, and germanium.

11 Claims, 1 Drawing Sheet

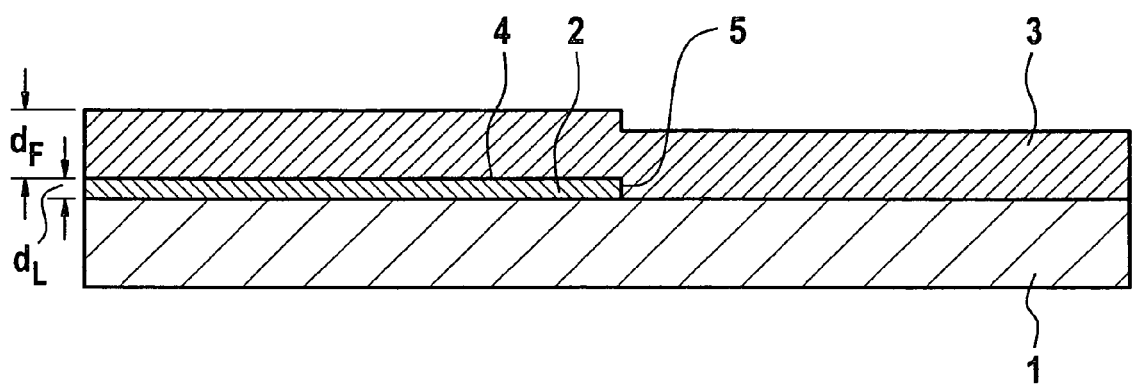

US 9,080,967 B2

ELECTRONIC COMPONENT FOR HIGH TEMPERATURES

BACKGROUND OF THE INVENTION

1. Field of the Invention

The present invention relates to an electronic component for high temperatures, in particular a chemically sensitive semiconductor component.

2. Description of the Related Art

Electronic components may have a substrate, a conductor track structure situated on the substrate and a functional layer which is contacted via the conductor track structure, it being possible for the conductor track structure to be partially covered by the functional layer for contacting the functional layer.

For example, an electronic component of this type may be a chemically sensitive, for example a gas-sensitive, field effect transistor sensor. The functional layer may be the gate electrode of the field effect transistor. The conductor track structure is usually made of pure platinum.

If a chemically sensitive field effect transistor sensor is used to detect gas components in an exhaust gas of an internal combustion engine, for example an internal combustion engine of a motor vehicle, the chemically sensitive field effect transistor is, however, exposed to a chemically aggressive, in particular oxidative, atmosphere and temperatures above 500° C.

Under these conditions, pure platinum may degrade, in particular shrink, and the conductor track structure may be severed. Conductor track structures made of platinum are therefore usually much thicker than the functional layer. However, this may result in the functional layer becoming severed on the vertical surfaces of the conductor track structure.

BRIEF SUMMARY OF THE INVENTION

The present invention provides an electronic component, in particular a semiconductor component, which includes a substrate, a conductor track structure situated on the substrate, and a functional layer which is contacted via the conductor track structure. According to the present invention, the conductor track structure is made of a metal mixture which includes platinum and one or more metals selected from the group made up of rhodium, iridium, ruthenium, palladium, osmium, gold, scandium, yttrium, lanthanum, the lanthanides, titanium, zirconium, hafnium, niobium, tantalum, chromium, tungsten, rhenium, iron, cobalt, nickel, copper, boron, aluminum, gallium, indium, silicon, and germanium.

BRIEF DESCRIPTION OF THE DRAWING

FIG. 1 shows a schematic cross section of an example embodiment of an electronic component according to the present invention.

DETAILED DESCRIPTION OF THE INVENTION

FIG. 1 shows that the electronic component includes a substrate 1, a conductor track structure 2 situated on substrate 1 and a functional layer 3 which is contacted via conductor track structure 2. To contact functional layer 3, conductor path structure 2 is covered by functional layer 3. Functional layer 3 partially covers conductor track structure 2 and partially covers substrate 1.

FIG. 1 further shows that conductor track structure 2 has a thickness $d_L$ which is less than thickness $d_F$ of functional layer 3. In particular, thickness $d_L$ of conductor track structure 2 is less than 50% of thickness $d_F$ of functional layer 3. FIG. 1 illustrates the fact that severing of the functional layer at the transition between conductor track 2 and substrate 1 may be prevented thereby. In particular, FIG. 1 illustrates the fact that both cover surface 4 and side surfaces 5 of conductor track structure 2 are covered by functional layer 3 in this way.

The conductor track structure made of a metal mixture according to the present invention has the advantage that the resistance of the conductor track structure to a chemically aggressive, in particular oxidative, atmosphere at high temperatures from 400° C. to 1,000° C., for example from 500° C. to 800° C., may be improved. In this way, the conductor track structure may be provided with a thinner design than conventional conductor track structures made of pure platinum. In particular, the conductor track structure may be designed in this way to be thinner than the functional layer. This, in turn, may prevent a functional layer which partially covers the conductor track from becoming severed.

Within the scope of the present invention, the semimetals, for example boron, silicon, germanium, are counted among the metals.

For the purpose of the present invention, the "lanthanides" are understood to be, in particular, the following elements: cerium, praseodymium, neodymium, promethium, samarium, europium, gadolinium, terbium, dysprosium, holmium, erbium, thulium, ytterbium, and lutetium.

Platinum is preferably the main component of the metal mixture. "The main component of the metal mixture" may be understood to be, in particular, the metal in the metal mixture which has the highest mole percentage of the metals in the metal mixture.

The metal mixture may be made up of, in particular, platinum and one or more metals selected from the group made up of rhodium, iridium, ruthenium, palladium, osmium, gold or scandium, yttrium, lanthanum, the lanthanides, titanium, zirconium, hafnium, niobium, tantalum, chromium, tungsten, rhenium, iron, cobalt, nickel, copper, boron, aluminum, gallium, indium, silicon, and germanium.

The metal mixture may include or may be made up of, for example, platinum and one or more metals selected from the group made up of rhodium, iridium, ruthenium, palladium, osmium, and gold.

Alternatively, the metal mixture may include or may be made up of platinum and one or more metals selected from the group made up of scandium, yttrium, lanthanum, the lanthanides, titanium, zirconium, hafnium, niobium, tantalum, chromium, tungsten, rhenium, iron, cobalt, nickel, copper, boron, aluminum, gallium, indium, silicon, and germanium.

Within the scope of a specific embodiment, the metal mixture includes platinum and one or more metals selected from the group made up of titanium, zirconium, hafnium, chromium, rhenium and aluminum, and/or one or more metals selected from the group made up of rhodium, iridium, and ruthenium.

The metal mixture preferably includes or is made up of platinum and rhodium.

Within the scope of a further specific embodiment, the metal mixture includes from ≥60 atom percent to ≤99 atom percent, in particular from ≥75 atom percent to ≤90 atom percent, of platinum and from ≥1 atom percent to ≤40 atom percent, in particular from ≥10 atom percent to ≤25 atom percent of one or more metals selected from the group made up of rhodium, iridium, ruthenium, palladium, osmium, gold, scandium, yttrium, lanthanum, the lanthanides, titanium, zirconium, hafnium, niobium, tantalum, chromium, tungsten, rhenium, iron, cobalt, nickel, copper, boron, aluminum, gallium, indium, silicon, and germanium, the sum of the atoms of platinum rhodium, iridium, ruthenium, palladium, osmium, gold, scandium, yttrium, lanthanum, the lanthanides, titanium, zirconium, hafnium, niobium, tantalum, chromium, tungsten, rhenium, iron, cobalt, nickel, copper, boron, aluminum, gallium, indium, silicon, and germanium together resulting in 100 atom percent.

In particular, the metal mixture may include from ≥60 atom percent to ≤99 atom percent, in particular from ≥75 atom percent to ≤90 atom percent, of platinum and from ≥1 atom percent to ≤40 atom percent, in particular from ≥10 atom percent to ≤25 atom percent, of one or more metals selected from the group made up of rhodium, iridium, ruthenium titanium, zirconium, hafnium, chromium, rhenium and aluminum, the sum of the atoms of platinum, rhodium, iridium, ruthenium titanium, zirconium, hafnium, chromium, rhenium and aluminum together resulting in 100 atom percent.

For example, the metal mixture may include from ≥60 atom percent to ≤99 atom percent, in particular from ≥75 atom percent to ≤90 atom percent, of platinum and from ≥1 atom percent to ≤40 atom percent, in particular from ≥10 atom percent to ≤25 atom percent, of one or more metals selected from the group made up of titanium, zirconium, hafnium, chromium, rhenium and aluminum, the sum of the atoms of platinum, titanium, zirconium, hafnium, chromium, rhenium and aluminum together resulting in 100 atom percent.

As an alternative thereto, the metal mixture may include from ≥60 atom percent to ≤99 atom percent, in particular from ≥75 atom percent to ≤90 atom percent, of platinum and from ≥1 atom percent to ≤40 atom percent, in particular from ≥10 atom percent to ≤25 atom percent, of one or more metals selected from the group made up of rhodium, iridium and ruthenium, the sum of the atoms of platinum, rhodium, iridium and ruthenium together resulting in 100 atom percent.

Within the scope of a further specific embodiment, the metal mixture includes from ≥60 atom percent to ≤99 atom percent, in particular from ≥75 atom percent to ≤90 atom percent, of platinum and from ≥1 atom percent to ≤40 atom percent, in particular from ≥10 atom percent to ≤25 atom percent, of rhodium, the sum of the atoms of platinum and rhodium together resulting in 100 atom percent.

Within the scope of a further specific embodiment, the metal mixture is a metal alloy.

Within the scope of a further specific embodiment, the metal mixture includes platinum cores, each of which is at least partially surrounded, in particular essentially completely surrounded, by a metal layer made of one or more metals selected from the group made up of rhodium, iridium, ruthenium, palladium, osmium, gold, scandium, yttrium, lanthanum, the lanthanides, titanium, zirconium, hafnium, niobium, tantalum, chromium, tungsten, rhenium, iron, cobalt, nickel, copper, boron, aluminum, gallium, indium, silicon, and germanium, in particular rhodium. By surrounding the platinum cores with a metal layer of this type, it is possible, if necessary, to prevent or at least reduce platinum evaporation or agglomeration. "Essentially completely surrounded" is understood to mean that, in particular, deviations based on the fact that two or more cores contact each other and/or that a core or multiple cores contact the surface of the substrate are included. The platinum cores may have, for example, an average size from ≥0.1 nm to ≤90 nm, in particular from ≥3 nm to ≤50 nm, for example from ≥5 nm to ≤20 nm, measured using scanning electron microscopy. The metal layer may have, for example, a layer thickness from ≥0.1 nm to ≤90 nm, in particular from ≥3 nm to ≤50 nm, for example from ≥5 nm to ≤20 nm, measured using scanning electron microscopy.

To contact the functional layer, the conductor path structure may be partially covered by the functional layer.

Within the scope of a further specific embodiment, the functional layer partially covers the conductor track structure and partially covers the substrate.

The functional layer may be a porous and/or electrically conductive layer. "Electrically conductive" is understood to mean, in particular, that the layer has a specific conductivity of at least $10 \text{ Sm}^{-1}$. The functional layer may include pores having an average pore size from ≥0.2 nm to 20 nm, in particular from ≥0.3 nm to ≤10 nm, for example from ≥0.5 nm to ≤5 nm, measured using scanning electron microscopy. For example, the functional layer may be made of a material selected from the group made up of platinum, rhodium, iridium, ruthenium, palladium, osmium, gold, scandium, yttrium, lanthanum, the lanthanides, titanium, zirconium, hafnium, niobium, tantalum, chromium, tungsten, rhenium, iron, cobalt, nickel, copper, boron, aluminum, gallium, indium, silicon, and germanium, metal mixtures of these metals, in particular alloys of these metals, combinations of one or more of these metals with oxygen, nitrogen and/or carbon, as well as mixtures of one or more of these metals with one or more combinations of these metals with oxygen, nitrogen and/or carbon. In particular, the functional layer may be made of the same metal mixture as the conductor track structure.

Within the scope of a further specific embodiment, the conductor track structure has a thickness ($d_L$) which is less than the thickness ($d_F$) of the functional layer. The danger of a functional layer covering the conductor track structure being severed may be reduced in this manner.

Within the scope of a further specific embodiment, the conductor track structure has a thickness ($d_L$) from ≥0.5 nm to ≤100 nm, in particular from ≥5 nm to ≤50 nm, for example approximately 20 nm. Due to a thin conductor track structure of this type, it is possible, on the one hand, to reduce warping. On the other hand, conductor track structures of this type may be designed to be thinner than the functional layer, which may reduce the danger of a functional layer covering the conductor structure being severed.

Within the scope of a further specific embodiment, the functional layer has a thickness ($d_F$) from ≥1 nm to ≤200 nm, in particular from ≥10 nm to ≤100 nm, for example approximately 50 nm.

The thickness ($d_L$) of the conductor track structure may have a ratio of, for example, 1:5 to 1:2 to the thickness ($d_F$) of the functional layer.

Within the scope of a further specific embodiment, the thickness ($d_L$) of the conductor track structure is less than 50% of the thickness ($d_F$) of the functional layer. This has the advantage that the severance of a functional layer covering the conductor track structure may be avoided.

The conductor path structure may be applied to the substrate or structured on the substrate, for example using vapor deposition and/or sputtering methods. Methods of this type are described, for example, in the publication: "A study of platinum electrode patterning in a reactive ion etcher," J. Vac. Sci. Technol. A 16(3), May/June 1998, pages 1489 through 1496.

The substrate may be made, for example, of sapphire or silicon dioxide.

Within the scope of a further specific embodiment, the electronic component is a chemically sensitive, in particular gas-sensitive, semiconductor component, for example a chemically sensitive field effect transistor, for example a chemically sensitive field effect transistor sensor. In particular, the semiconductor component may be designed for measuring one or more gas components, for example hydrocarbons, carbon monoxide, carbon dioxide, water, ammonia and/or nitrogen oxides such as nitrogen monoxide and/or nitrogen dioxide, for example in an exhaust gas of an internal combustion engine, such as an internal combustion engine of a motor vehicle.

Within the scope of a further specific embodiment, the functional layer is a gate electrode or an integral part of a gate electrode of a field effect transistor.

A further subject matter of the present invention is the use of a metal mixture, which includes platinum and one or more metals selected from the group made up of rhodium, iridium, ruthenium, palladium, osmium, gold, scandium, yttrium, lanthanum, the lanthanides, titanium, zirconium, hafnium, niobium, tantalum, chromium, tungsten, rhenium, iron, cobalt, nickel, copper, boron, aluminum, gallium, indium, silicon, and germanium, as the conductor track material for a chemically sensitive, in particular gas-sensitive, semiconductor component, for example a chemically sensitive field effect transistor, for example a chemically sensitive field effect transistor sensor. In particular, the semiconductor component may be designed for measuring one or more gas components, for example hydrocarbons, carbon monoxide, carbon dioxide, water, ammonia and/or nitrogen oxides such as nitrogen monoxide and/or nitrogen dioxide, for example in an exhaust gas of an internal combustion engine, such as an internal combustion engine of a motor vehicle.

The metal mixture preferably includes
from ≥60 atom percent to ≤99 atom percent, in particular from ≥75 atom percent to ≤90 atom percent, of platinum an
from ≥1 atom percent to ≤40 atom percent, in particular from ≥10 atom percent to ≤25 atom percent, of rhodium, the sum of the platinum and rhodium atoms together resulting in 100 atom percent.

With regard to further composition variants and embodiments of the metal mixture, reference is hereby made explicitly to the preceding disclosure in connection with the electronic component.

What is claimed is:

1. An electronic component, comprising:
    a substrate;
    a conductor track structure situated on the substrate; and
    a functional layer which is contacted via the conductor track structure;
    wherein the conductor track structure is made of a metal mixture including platinum cores and at least one metal selected from the group made up of rhodium, iridium, ruthenium, palladium, osmium, gold, scandium, yttrium, lanthanum, the lanthanides, titanium, zirconium, hafnium, niobium, tantalum, chromium, tungsten, rhenium, iron, cobalt, nickel, copper, boron, aluminum, gallium, indium, silicon, and germanium; and
    wherein:
        each platinum core is contacted by another metal that forms the at least one metal;
        the platinum cores are particles; and
        at least some of the particles include multiple platinum atoms.

2. The electronic component as recited in claim 1, wherein one metal that forms the at least one metal is selected from the group made up of titanium, zirconium, hafnium, chromium, rhenium, and aluminum; and a second metal that forms the at least one metal is selected from the group made up of rhodium, iridium, and ruthenium.

3. The electronic component as recited in claim 1, wherein the metal mixture includes:
    (i) a first component formed by the platinum cores, the first component including from ≥60 atom percent to ≤99 atom percent of platinum; and
    (ii) a second component formed by the at least one metal, the second component including from ≥1 atom percent to ≤40 atom percent of the at least one metal;
    wherein the sum of the first and second components is 100 atom percent.

4. The electronic component as recited in claim 3, wherein the second component includes from ≥1 atom percent to ≤40 atom percent of rhodium, and wherein the sum of the platinum and rhodium atoms together result in 100 atom percent.

5. The electronic component as recited in claim 3, wherein the functional layer partially covers the conductor track structure and partially covers the substrate.

6. The electronic component as recited in claim 3, wherein the conductor track structure has a thickness which is less than the thickness of the functional layer.

7. The electronic component as recited in claim 3, wherein at least one of: (i) the conductor track structure has a thickness from ≥0.5 nm to ≤100 nm; and (ii) the functional layer has a thickness from ≥1 nm to ≤200 nm.

8. The electronic component as recited in claim 6, wherein the thickness of the conductor track structure is less than 50% of the thickness of the functional layer.

9. The electronic component as recited in claim 6, wherein the electronic component forms part of a chemically sensitive field effect transistor sensor.

10. The electronic component as recited in claim 9, wherein the functional layer is one of a gate electrode or an integral part of a gate electrode of the field effect transistor.

11. The electronic component as recited in claim 1, wherein the conductor track structure includes a side surface oriented along a thickness direction of the conductor track structure, the side surface is completely covered by the functional layer, and the thickness of the conductor track structure is less than the thickness of the functional layer.

\* \* \* \* \*